(12) United States Patent
Klemm et al.

(10) Patent No.: US 9,352,062 B2
(45) Date of Patent: May 31, 2016

(54) WEARABLE CHEMICAL DISPENSER

(71) Applicant: S.C. Johnson & Son, Inc., Racine, WI (US)

(72) Inventors: Robert W. Klemm, Colgate, WI (US); Nitin Sharma, Kenosha, WI (US); Cathal L. Fahy, Racine, WI (US); Deliang Shi, Kenosha, WI (US)

(73) Assignee: S.C. Johnson & Son, Inc., Racine, WI (US)

( * ) Notice: Subject to any disclaimer, the term of this patent is extended or adjusted under 35 U.S.C. 154(b) by 156 days.

(21) Appl. No.: 14/067,241

(22) Filed: Oct. 30, 2013

(65) Prior Publication Data

US 2015/0115060 A1    Apr. 30, 2015

(51) Int. Cl.
*B01D 47/16* (2006.01)
*A61L 9/12* (2006.01)
*A01M 1/20* (2006.01)

(52) U.S. Cl.
CPC .............. *A61L 9/122* (2013.01); *A01M 1/2033* (2013.01); *A01M 1/2055* (2013.01); *A61L 2209/133* (2013.01); *A61L 2209/134* (2013.01)

(58) Field of Classification Search
CPC ......... A24F 25/00; B01D 47/16; A61L 9/122; A61L 2009/133; A61L 2009/134; A01M 1/02; A01M 1/2022
USPC ............ 239/101–102.2, 152, 332, 55, 57, 60; 422/124, 120
See application file for complete search history.

(56) References Cited

U.S. PATENT DOCUMENTS

| | | |
|---|---|---|
| 2,585,339 A | 2/1952 | Miller |
| 2,614,820 A | 10/1952 | Boydjieff |
| 2,764,789 A | 10/1956 | Zelenka |
| 3,633,881 A | 1/1972 | Yurdin |
| 4,059,422 A | 11/1977 | Steiner |
| 4,111,655 A | 9/1978 | Quincey |
| 4,166,087 A | 8/1979 | Cline |
| 4,268,285 A | 5/1981 | Mason |
| 4,294,778 A | 10/1981 | DeLuca |

(Continued)

FOREIGN PATENT DOCUMENTS

| | | |
|---|---|---|
| CN | 103007326 A | 4/2013 |
| DE | 202009009540 U1 | 11/2009 |

(Continued)

OTHER PUBLICATIONS

Wolfram Alpha, "AA battery," Wolfram Alpha LLC—A Wolfram Research Company. http://www.wolframalpha.com/input/?i=aa+battery&lk=4.*

(Continued)

*Primary Examiner* — Arthur O Hall
*Assistant Examiner* — Joseph A Greenlund (57) ABSTRACT

Wearable devices for dispensing insect repellents, fragrances, and/or other chemicals along the outside of the clothing of a human are disclosed. They are of the type that are clipped onto a belt or the like, and use a powered fan to dispense active. They are configured with outlet arrangements to minimize power use while still achieving acceptable air flow rates. These changes permit use of smaller power supplies and more compact arrangements for power supply (e.g., battery) positioning. This in turn permits a much more compact and lightweight construction to achieve the desired results.

20 Claims, 10 Drawing Sheets

(56) References Cited

U.S. PATENT DOCUMENTS

| | | |
|---|---|---|
| 4,301,095 A | 11/1981 | Mettler |
| 4,377,399 A | 3/1983 | Bryson |
| 4,396,557 A | 8/1983 | DeLuca |
| 4,432,938 A * | 2/1984 | Meetze, Jr. ............ A61L 9/122 261/101 |
| 4,830,791 A | 5/1989 | Muderlak |
| 4,931,224 A | 6/1990 | Holzner, Sr. |
| 5,126,078 A | 6/1992 | Steiner |
| 5,147,582 A | 9/1992 | Holzner, Sr. |
| 5,193,984 A | 3/1993 | Lin |
| 5,234,162 A | 8/1993 | Sullivan |
| 5,305,541 A | 4/1994 | Simpson |
| 5,342,584 A * | 8/1994 | Fritz .................... A61L 9/122 206/807 |
| 5,358,443 A | 10/1994 | Mitchell |
| 5,370,829 A | 12/1994 | Kunze |
| 5,431,885 A | 7/1995 | Zlotnik |
| 5,435,817 A | 7/1995 | Davis |
| 5,498,397 A | 3/1996 | Horng |
| 5,547,616 A | 8/1996 | Dancs |
| 5,562,407 A | 10/1996 | Cielo |
| 5,616,172 A | 4/1997 | Tuckerman |
| 5,620,306 A | 4/1997 | Day |
| 5,641,343 A | 6/1997 | Frey |
| 5,695,692 A | 12/1997 | Kennedy |
| 5,735,918 A | 4/1998 | Barradas |
| 5,753,000 A | 5/1998 | Chiu |
| 5,829,188 A | 11/1998 | Tanitomi |
| 5,837,020 A | 11/1998 | Cartellone |
| 5,840,092 A | 11/1998 | Rick |
| 5,925,172 A | 7/1999 | Rick |
| 5,932,147 A | 8/1999 | Chen |
| 6,042,333 A | 3/2000 | Day |
| 6,050,016 A | 4/2000 | Cox |
| 6,050,551 A | 4/2000 | Anderson |
| 6,061,950 A | 5/2000 | Carey |
| 6,102,660 A | 8/2000 | Lee |
| 6,103,201 A | 8/2000 | Green |
| 6,106,786 A | 8/2000 | Akahoshi |
| 6,154,607 A | 11/2000 | Flashinski |
| 6,156,085 A | 12/2000 | Chiu |
| 6,156,088 A | 12/2000 | Cardarelli |
| 6,192,621 B1 | 2/2001 | Fain |
| 6,241,218 B1 | 6/2001 | Tanitomi |
| 6,254,065 B1 | 7/2001 | Ehrensperger |
| 6,293,044 B1 | 9/2001 | Feng |
| 6,315,821 B1 | 11/2001 | Pillion |
| 6,328,791 B1 | 12/2001 | Pillion |
| 6,361,752 B1 | 3/2002 | Demarest |
| 6,371,450 B1 | 4/2002 | Davis |
| 6,391,329 B1 | 5/2002 | Ito |
| 6,392,549 B1 | 5/2002 | Wu |
| 6,435,828 B1 | 8/2002 | Bostwick |
| 6,447,587 B1 | 9/2002 | Pillion |
| 6,482,365 B1 | 11/2002 | Soller |
| 6,497,753 B1 | 12/2002 | Gutmann |
| 6,508,868 B2 | 1/2003 | Pillion |
| 6,511,531 B1 | 1/2003 | Cartellone |
| 6,514,052 B2 | 2/2003 | Bostwick |
| 6,553,711 B1 | 4/2003 | Feng |
| 6,569,387 B1 | 5/2003 | Furner |
| 6,592,104 B2 | 7/2003 | Cox |
| 6,610,254 B1 | 8/2003 | Furner |
| 6,623,265 B1 | 9/2003 | Day |
| 6,631,888 B1 | 10/2003 | Prueter |
| 6,632,405 B2 | 10/2003 | Lua |
| 6,719,217 B1 | 4/2004 | Tawara |
| 6,769,631 B2 | 8/2004 | Brown |
| 6,783,081 B2 | 8/2004 | Pedrotti |
| 6,783,117 B2 | 8/2004 | Wohrle |
| 6,857,214 B1 | 2/2005 | Pelissier |
| 6,881,382 B2 | 4/2005 | Goldstein |
| 6,899,931 B2 | 5/2005 | Porchia |
| 6,909,840 B2 | 6/2005 | Harwig |
| 6,913,733 B2 | 7/2005 | Hardy |
| 6,926,902 B2 * | 8/2005 | Inoue .................. A01M 1/2033 424/405 |
| 6,950,607 B2 | 9/2005 | Yip |
| 6,966,665 B2 | 11/2005 | Limburg |
| 7,007,861 B2 | 3/2006 | Ketcha |
| 7,008,180 B2 | 3/2006 | Fujimori |
| 7,040,548 B2 | 5/2006 | Rodgers |
| 7,112,232 B2 | 9/2006 | Chang |
| 7,132,084 B1 | 11/2006 | Roumpos |
| 7,138,130 B2 | 11/2006 | Davis |
| 7,152,809 B2 | 12/2006 | Ketcha |
| 7,167,641 B2 | 1/2007 | Tam |
| 7,168,630 B1 | 1/2007 | Ketcha |
| 7,175,815 B2 * | 2/2007 | Yamasaki ........... A01M 1/2033 261/31 |
| 7,188,783 B2 | 3/2007 | Ivey |
| 7,204,870 B2 | 4/2007 | Zobele |
| 7,285,248 B2 | 10/2007 | Yamamoto |
| 7,316,729 B2 | 1/2008 | Paterson |
| 7,341,698 B2 | 3/2008 | Pedrotti |
| 7,344,123 B2 | 3/2008 | Pankhurst |
| 7,431,901 B2 | 10/2008 | Stiros |
| 7,455,245 B2 * | 11/2008 | Sipinski .............. A01M 1/205 239/102.2 |
| 7,459,168 B2 | 12/2008 | Inoue |
| 7,476,002 B2 | 1/2009 | Wolf |
| 7,481,571 B2 | 1/2009 | Bistritzky |
| 7,484,716 B2 | 2/2009 | Ford Morie |
| 7,484,860 B2 | 2/2009 | Demarest |
| 7,503,675 B2 | 3/2009 | Demarest |
| 7,585,344 B2 | 9/2009 | Paterson |
| 7,597,308 B1 | 10/2009 | Stucki |
| 7,597,857 B2 | 10/2009 | Reece |
| 7,621,511 B2 | 11/2009 | Hayes-Pankhurst |
| 7,641,364 B2 | 1/2010 | Abbondanzio |
| 7,670,035 B2 | 3/2010 | Tsai |
| 7,748,687 B2 | 7/2010 | Pankhurst |
| 7,811,348 B2 | 10/2010 | Paterson |
| 7,833,492 B2 | 11/2010 | Schumacher |
| 7,887,759 B2 | 2/2011 | Triplett |
| 7,887,760 B2 * | 2/2011 | Yamamoto .......... A01M 1/2033 422/124 |
| 7,892,487 B2 | 2/2011 | Adair |
| 7,917,018 B2 | 3/2011 | Schumacher |
| 7,959,132 B2 | 6/2011 | Butler |
| 8,025,845 B2 | 9/2011 | Yamasaki |
| 8,048,379 B2 | 11/2011 | Sassoon |
| 8,074,970 B2 | 12/2011 | Pankhurst |
| 8,137,629 B2 | 3/2012 | Faber |
| 8,197,761 B1 | 6/2012 | Miller-Larry |
| 8,282,883 B2 | 10/2012 | Yamasaki |
| 8,303,385 B2 | 11/2012 | Park |
| 8,328,894 B2 * | 12/2012 | Thurin ................ F24F 3/1603 55/467 |
| 8,347,549 B2 | 1/2013 | Durand |
| 8,359,785 B2 * | 1/2013 | Ohtsuka ............. A01M 1/2033 43/138 |
| 8,367,011 B2 | 2/2013 | Yamamoto |
| 8,371,740 B2 | 2/2013 | Pestl |
| 8,385,730 B2 | 2/2013 | Bushman |
| 8,435,450 B2 | 5/2013 | Kawamura |
| 8,449,828 B2 | 5/2013 | Yamamoto |
| 8,524,158 B2 * | 9/2013 | Shi ..................... A01M 1/2033 239/55 |
| 8,551,409 B2 | 10/2013 | Yamamoto |
| 8,603,397 B2 | 12/2013 | Gruenbacher |
| 8,807,538 B2 * | 8/2014 | Sharma .............. A01M 1/2044 261/104 |
| 8,944,342 B2 * | 2/2015 | Maget ................. A61L 9/12 222/1 |
| 2002/0197189 A1 | 12/2002 | Lua |
| 2003/0012680 A1 | 1/2003 | Balsys |
| 2003/0175171 A1 * | 9/2003 | Yamamoto .......... A01M 1/2033 422/124 |
| 2004/0146435 A1 | 7/2004 | Goldstein et al. |
| 2005/0019165 A1 | 1/2005 | Fujimori et al. |
| 2005/0191217 A1 | 9/2005 | Selander |
| 2005/0214175 A1 | 9/2005 | Barker |
| 2005/0220664 A1 | 10/2005 | Hitzler et al. |

(56) References Cited

U.S. PATENT DOCUMENTS

| | | |
|---|---|---|
| 2005/0226788 A1 | 10/2005 | Hrybyk et al. |
| 2005/0255008 A1 | 11/2005 | Lin |
| 2006/0039835 A1 | 2/2006 | Nottingham et al. |
| 2006/0043619 A1 | 3/2006 | Brown et al. |
| 2006/0137241 A1 | 6/2006 | Yamasaki et al. |
| 2007/0001024 A1 | 1/2007 | Wold et al. |
| 2007/0036673 A1 | 2/2007 | Selander |
| 2007/0036688 A1* | 2/2007 | Hayes-Pankhurst ... A45D 34/02 422/124 |
| 2007/0087679 A1 | 4/2007 | Yamasaki et al. |
| 2007/0111654 A1 | 5/2007 | Yamasaki et al. |
| 2007/0158456 A1 | 7/2007 | Spector |
| 2007/0180801 A1 | 8/2007 | Paterson et al. |
| 2007/0180996 A1 | 8/2007 | Paterson et al. |
| 2008/0130266 A1 | 6/2008 | DeWitt et al. |
| 2008/0244954 A1 | 10/2008 | Shannon |
| 2008/0271338 A1 | 11/2008 | Muir et al. |
| 2008/0299014 A1 | 12/2008 | Kim |
| 2009/0008411 A1 | 1/2009 | Schumacher et al. |
| 2009/0060799 A1 | 3/2009 | Torres |
| 2009/0072783 A1 | 3/2009 | Gaspar et al. |
| 2009/0183636 A1 | 7/2009 | Levine et al. |
| 2009/0200393 A1 | 8/2009 | Avelar |
| 2010/0025490 A1 | 2/2010 | Bushman et al. |
| 2010/0044468 A1 | 2/2010 | Granger et al. |
| 2010/0064895 A1 | 3/2010 | Thurin et al. |
| 2010/0090022 A1 | 4/2010 | Hayashida |
| 2010/0129268 A1* | 5/2010 | Andersen ............... G06Q 99/00 422/124 |
| 2010/0132246 A1 | 6/2010 | Ohtsuka et al. |
| 2010/0150774 A1 | 6/2010 | Marchetti et al. |
| 2010/0177597 A1 | 7/2010 | Tsai |
| 2010/0180830 A1 | 7/2010 | Fritter et al. |
| 2010/0269826 A1 | 10/2010 | Colombo et al. |
| 2010/0284783 A1 | 11/2010 | Lolmede |
| 2010/0288847 A1 | 11/2010 | Gruenbacher et al. |
| 2011/0027124 A1* | 2/2011 | Albee ..................... A61L 9/122 422/5 |
| 2011/0038761 A1* | 2/2011 | Saleh ................. A01M 1/2033 422/124 |
| 2011/0049259 A1 | 3/2011 | Beland et al. |
| 2011/0108633 A1 | 5/2011 | Yamamoto et al. |
| 2011/0108634 A1 | 5/2011 | Yamamoto et al. |
| 2011/0110827 A1 | 5/2011 | Yamamoto et al. |
| 2011/0116977 A1 | 5/2011 | Yamamoto et al. |
| 2011/0134628 A1 | 6/2011 | Pestl et al. |
| 2011/0221079 A1 | 9/2011 | Yamasaki et al. |
| 2011/0268605 A1 | 11/2011 | Haran |
| 2012/0180666 A1 | 7/2012 | Lim et al. |
| 2012/0181350 A1 | 7/2012 | Snider |
| 2012/0183280 A1 | 7/2012 | Kowalec et al. |
| 2012/0205460 A1 | 8/2012 | Franks |
| 2012/0248136 A1 | 10/2012 | Meyers |
| 2012/0261484 A2 | 10/2012 | Blaylock et al. |
| 2012/0273978 A1 | 11/2012 | Sharma |
| 2012/0275932 A1* | 11/2012 | Sharma ............... A01M 1/2044 417/66 |
| 2012/0288414 A1 | 11/2012 | Shi et al. |
| 2013/0049236 A1 | 2/2013 | Garon et al. |

FOREIGN PATENT DOCUMENTS

| | | |
|---|---|---|
| WO | 9846280 A2 | 10/1998 |
| WO | 9902032 A1 | 1/1999 |
| WO | 0165931 A1 | 9/2001 |
| WO | 02060246 A1 | 8/2002 |
| WO | 03103387 A2 | 12/2003 |
| WO | 2005063013 A1 | 7/2005 |
| WO | 2006052519 A2 | 5/2006 |
| WO | 2006084317 A1 | 8/2006 |
| WO | 2007017742 A1 | 2/2007 |
| WO | 2008112545 A1 | 9/2008 |
| WO | 2009065629 A1 | 5/2009 |
| WO | 2009092135 A1 | 7/2009 |
| WO | 2009111903 A1 | 9/2009 |
| WO | 2009147330 A1 | 12/2009 |
| WO | 2011019404 A2 | 2/2011 |
| WO | 2011106889 A1 | 9/2011 |
| WO | 2011126208 A2 | 10/2011 |
| WO | 2012131232 A1 | 10/2012 |
| WO | 2013032920 A1 | 3/2013 |

OTHER PUBLICATIONS

Wolfram Alpha, "AAA battery," Wolfram Alpha LLC—A Wolfram Research Company. http://www.wolframalpha.com/input/?i=aaa+battery.*

International Search Report and Written Opinion for PCT/US2014/062095 Dated May 15, 2015.

* cited by examiner

WEARABLE CHEMICAL DISPENSER

CROSS-REFERENCES TO RELATED APPLICATIONS

Not Applicable.

STATEMENT REGARDING FEDERALLY SPONSORED RESEARCH

Not Applicable.

BACKGROUND OF THE INVENTION

The present invention relates to wearable devices that dispense chemicals such as insect repellents and/or fragrances.

Various techniques have been developed to provide humans with protection from insect bites. For insect control inside buildings a primary emphasis is placed on trying to keep insects from entering the building at all (e.g. placing screens over windows). This sometimes is supplemented with chemical treatment of room air and/or the use of traps. See, for example, U.S. Pat. Nos. 6,582,714, 7,175,815, 7,621,511, and U.S. Patent Application Publication Nos. 2005/0079113, 2006/0039835, and 2006/0137241.

When the individual is outdoors where the area cannot be effectively screened, and the individual is mostly staying in a particular area (e.g. at a picnic, or on a patio near a building), traps and area-repellents are the primary focus.

Alternatively, when the individual is moving away from a single area that they control, individuals often apply a personal insect repellent to clothing or directly to their skin. However, some consumers have expressed a reluctance to apply insect repellents directly to their skin or to delicate clothing.

As a result, portable electrical devices having a fan and an insecticide source have been developed. These devices may have a clip so that they can easily be mounted on a belt, a purse, or even a pocket, and thus be "worn" by the consumer as they move outside. The device may draw air through, or blow air past, a substrate impregnated with an insect repellent or other air treatment chemical, thereby dispensing the active into the air, preferably (in the case of a repellent) along the outside of a human's clothing. See, for example, U.S. Pat. Nos. 6,926,902, 7,007,861, 7,152,809, 7,168,630, 7,175,815, 7,285,248, and 7,887,760, and U.S. Patent Application Publication No. 2009/0060799.

However, some such devices may blow the active too far out away from the human body, causing too little of the active to reach locations of primary concern (e.g. near ankles). Other such devices do not provide a way of minimizing waste of the active, such as while blower operation is suspended between uses. Still other such devices are unduly costly, are too heavy, or have other deficiencies.

The deficiencies in the above noted devices have been addressed by the wearable chemical dispensers described in U.S. Pat. Nos. 7,892,487, 7,833,492, and 7,917,018, and U.S. Patent Application Publication No. 2011/0038761. However, it is still desirable to improve this type of product further, particularly with respect to making the device more energy efficient.

Hence, a need still exists to improve wearable chemical dispensers in these areas.

SUMMARY OF THE INVENTION

In one aspect the invention provides a wearable device for dispensing an air treatment chemical. The device includes a housing including an inlet for permitting air to enter into an interior space of the housing and including a plurality of spaced apart outlets for permitting air mixed with air treatment chemical to exit the interior space; a substrate positioned within the housing wherein the substrate bears an air treatment chemical; a power supply mounted within a power supply compartment of the housing; a motor mounted within the housing wherein the motor is powered by the power supply; and a fan mounted within a fan compartment of the housing and connected to the motor wherein the fan is capable of moving air from the inlet adjacent the substrate so as to mix air treatment chemical into the moving air, and then deliver a mixture of air and air treatment chemical through the outlets to outside of the housing. The outlets are in fluid communication with the fan compartment of the housing. The outlets comprise a first array of openings on a first side of a longitudinal axis of the housing and the outlets also comprise a second array of openings on an opposite second side of the longitudinal axis of the housing. The first array of openings and the second array of openings are non-symmetric about the longitudinal axis of the housing.

In one form, the housing comprises a first side wall section on the first side of the longitudinal axis of the housing, a second side wall section on the second side of the longitudinal axis of the housing, a first end wall section connecting the first side wall section and the second side wall section, and a second end wall section connecting the first side wall section and the second side wall section. The first array of openings is located in the first side wall section and the first end wall section of the housing, and the second array of openings is located in the second side wall section and the first end wall section of the housing. The first array of openings and the second array of openings can be of generally uniform area.

In one form, the fan compartment is defined by the first side wall section of the housing, the second side wall section of the housing, the first end wall section of the housing, and a partition wall between the fan compartment and the power supply compartment, and a first end of the partition wall terminates at the first side wall section of the housing and an opposite second end of the partition wall terminates at the second end wall section of the housing. The first side wall section and the second side wall section of the housing can be generally straight, and the first end wall section and the second end wall section of the housing can be generally curved.

In one form of the dispenser, an included angle is defined by (i) a first location where the first end of the partition wall terminates at the first side wall section of the housing, (ii) a rotational axis of the fan, and (iii) a second location where the second end of the partition wall terminates at the second end wall section of the housing, and the included angle is less than 90 degrees. The mixture of air and air treatment chemical can be delivered through the outlets to outside of the housing at an ejection angle of greater than 270 degrees.

In one form, the fan compartment and the power supply compartment are in a side by side relationship coplanar with the longitudinal axis of the housing. The power supply compartment can include a recess for receiving the power supply wherein the recess has a major axis oriented at an oblique angle to the longitudinal axis of the housing. Preferably, the power supply is a single AA sized battery, and the recess is dimensioned to receive the battery.

In another aspect, the invention provides a wearable device for dispensing an air treatment chemical. The device includes a housing including an inlet for permitting air to enter into an interior space of the housing and including a plurality of spaced apart outlets for permitting air mixed with air treatment chemical to exit the interior space; a substrate positioned within the housing wherein the substrate bears an air treatment chemical; a power supply mounted within a power supply compartment of the housing; a motor mounted within the housing wherein the motor is powered by the power supply; and a fan mounted within a fan compartment of the housing and connected to the motor wherein the fan is capable of moving air from the inlet adjacent the substrate so as to mix air treatment chemical into the moving air, and then deliver a mixture of air and air treatment chemical through the outlets to outside of the housing. The outlets are in fluid communication with the fan compartment of the housing, and the power supply compartment includes a recess for receiving the power supply. The recess has a major axis oriented at an oblique angle to a longitudinal axis of the housing. The power supply can be a single AA sized battery, and the recess is dimensioned to receive the battery. Preferably, the device can maintain an average volumetric flow rate of air of at least 1.5 cubic feet per minute over a twelve hour period. More preferably, at least about 1.6 cubic feet per minute over a twelve hour period.

In one form of the dispenser, the fan compartment is defined by the first side wall section of the housing, the second side wall section of the housing, the first end wall section of the housing, and a partition wall between the fan compartment and the power supply compartment. A first end of the partition wall terminates at the first side wall section of the housing and an opposite second end of the partition wall terminates at the second end wall section of the housing. An included angle is formed by (i) a first location where the first end of the partition wall terminates at the first side wall section of the housing, (ii) a rotational axis of the fan, and (iii) a second location where the second end of the partition wall terminates at the second end wall section of the housing, and the included angle is less than 90 degrees. The mixture of air and air treatment chemical is delivered through the outlets to outside of the housing at an ejection angle of greater than 270 degrees.

In yet another aspect, the invention provides a wearable device for dispensing an air treatment chemical. The device includes a housing including an inlet for permitting air to enter into an interior space of the housing and including a plurality of spaced apart outlets for permitting air mixed with air treatment chemical to exit the interior space; a substrate positioned within the housing wherein the substrate bears an air treatment chemical; a power supply mounted within a power supply compartment of the housing; a motor mounted within the housing wherein the motor is powered by the power supply; and a fan mounted within a fan compartment of the housing and connected to the motor wherein the fan is capable of moving air from the inlet adjacent the substrate so as to mix air treatment chemical into the moving air, and then deliver a mixture of air and air treatment chemical through the outlets to outside of the housing. The fan compartment is defined by a first side wall section of the housing, a second side wall section of the housing, an end wall section of the housing, and a partition wall between the fan compartment and the power supply compartment. The outlets comprise openings in the first side wall section of the housing and the second side wall section of the housing, and the openings are in fluid communication with the fan compartment of the housing. The partition wall is dimensioned such that the fan compartment is in fluid communication with an additional number of openings in the second side wall section of the housing compared to the first side wall section of the housing.

In one form of the dispenser, the partition wall is a straight wall oriented at an oblique angle to a longitudinal axis of the housing. The power supply compartment can include a recess for receiving the power supply, and the recess has a major axis oriented at the oblique angle to the longitudinal axis of the housing.

In one form, a first end of the partition wall terminates at the first side wall section of the housing and an opposite second end of the partition wall terminates at the second end wall section of the housing. An included angle is defined by (i) a first location where the first end of the partition wall terminates at the first side wall section of the housing, (ii) a rotational axis of the fan, and (iii) a second location where the second end of the partition wall terminates at the second end wall section of the housing, and the included angle is less than 90 degrees. Preferably, the mixture of air and air treatment chemical delivered through the outlets to outside of the housing has an ejection angle of greater than 270 degrees.

It is an advantage of the invention to provide a wearable chemical dispenser having a more efficient air flow allowing the use of a lower energy battery which also yields a longer performance time.

These and other advantages of the present invention will become better understood upon consideration of the following detailed description, drawings, and claims.

BRIEF DESCRIPTION OF THE DRAWINGS

Like reference numerals will be used to refer to like parts from Figure to Figure in the following detailed description.

DETAILED DESCRIPTION OF THE INVENTION

A non-limiting example wearable chemical dispenser 18 is shown in FIGS. 1-11. The wearable chemical dispenser 18 includes a top housing section 20 having a generally oblong side wall 22 that extends from a top wall 23. In use, the top wall 23 is typically frontally disposed and acts as a lid. A plurality of spaced apart apertures 24 are radially arranged in the top wall 23 of the top housing section 20. The apertures 24 provide an inlet for permitting air to enter into an interior space of the wearable chemical dispenser 18. A tab 26 provides a means to grasp the top housing section 20 when opening the top housing section 20.

The wearable chemical dispenser 18 also includes a slide cover 28 having an on-off button 29, openings 31, and a cam projection 32. A fastener (e.g., a screw) or snap pawl(s) as shown mounts the slide cover 28 to the top housing section 20 such that the slide cover 28 can rotate with respect to the top housing section 20 when a user moves the on-off button 29 along the side wall 22 of the top housing section 20. In the 'off' position, the slide cover 28 closes the apertures 24 that are radially arranged in the top wall 23 of the top housing section 20. In the 'on' position, the openings 31 of the slide cover 28 align with the apertures 24 that are radially arranged in the top wall 23 of the top housing section 20.

Figure 1:
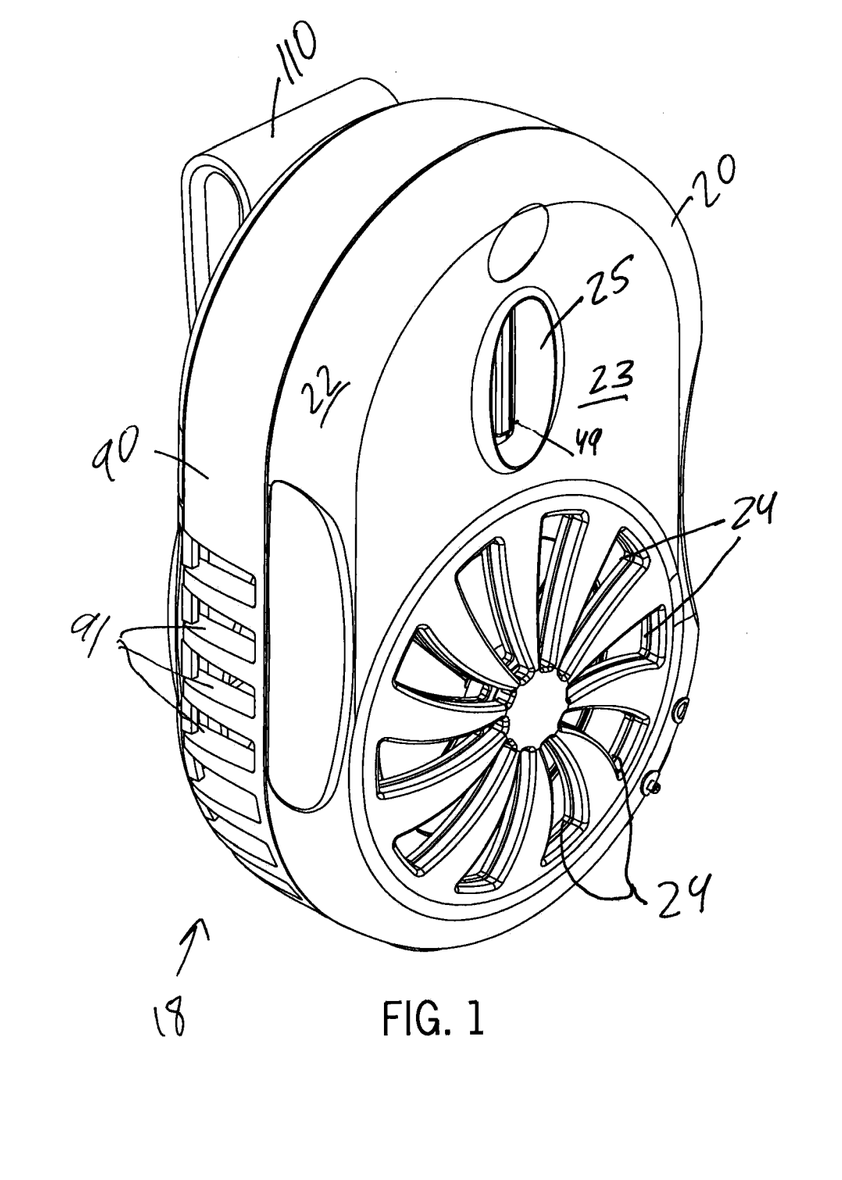
FIG. 1 is a left, top, front perspective view of a wearable chemical dispenser according to the invention.
Figures 2, 3:
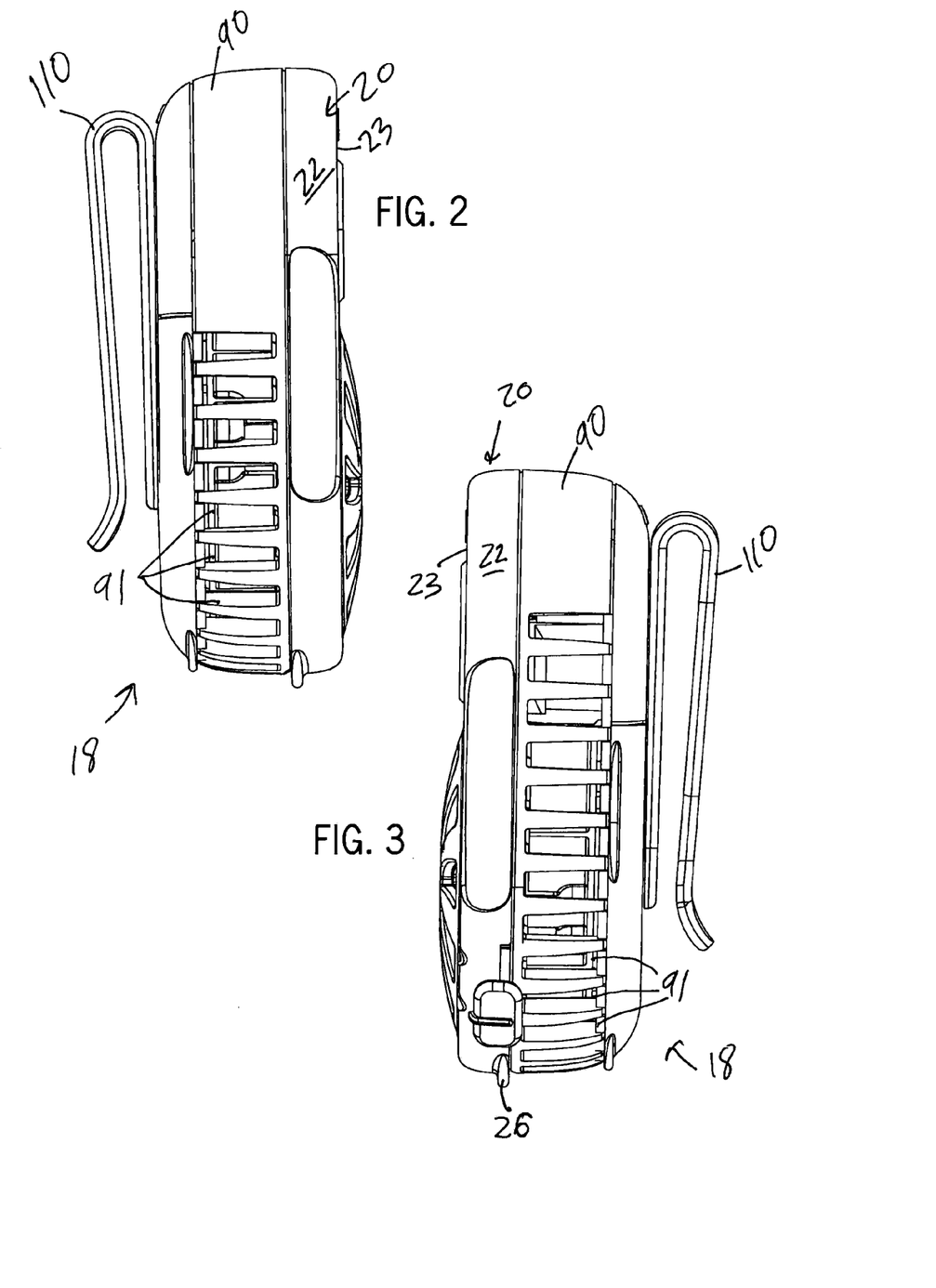
FIG. 2 is a left side elevational view of the dispenser of FIG. 1.
FIG. 3 is a right side elevational view of the dispenser of FIG. 1.
Figure 4:
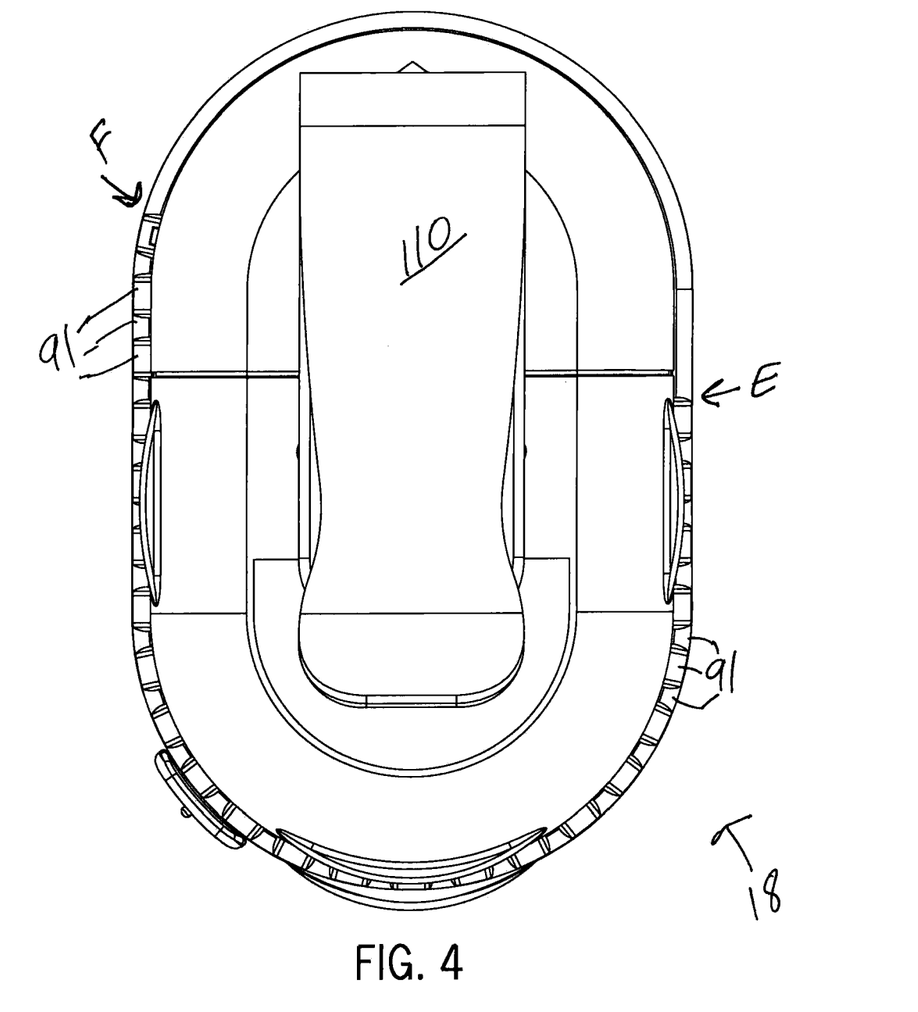
FIG. 4 is a rear elevational view of the dispenser of FIG. 1.
Figure 5:
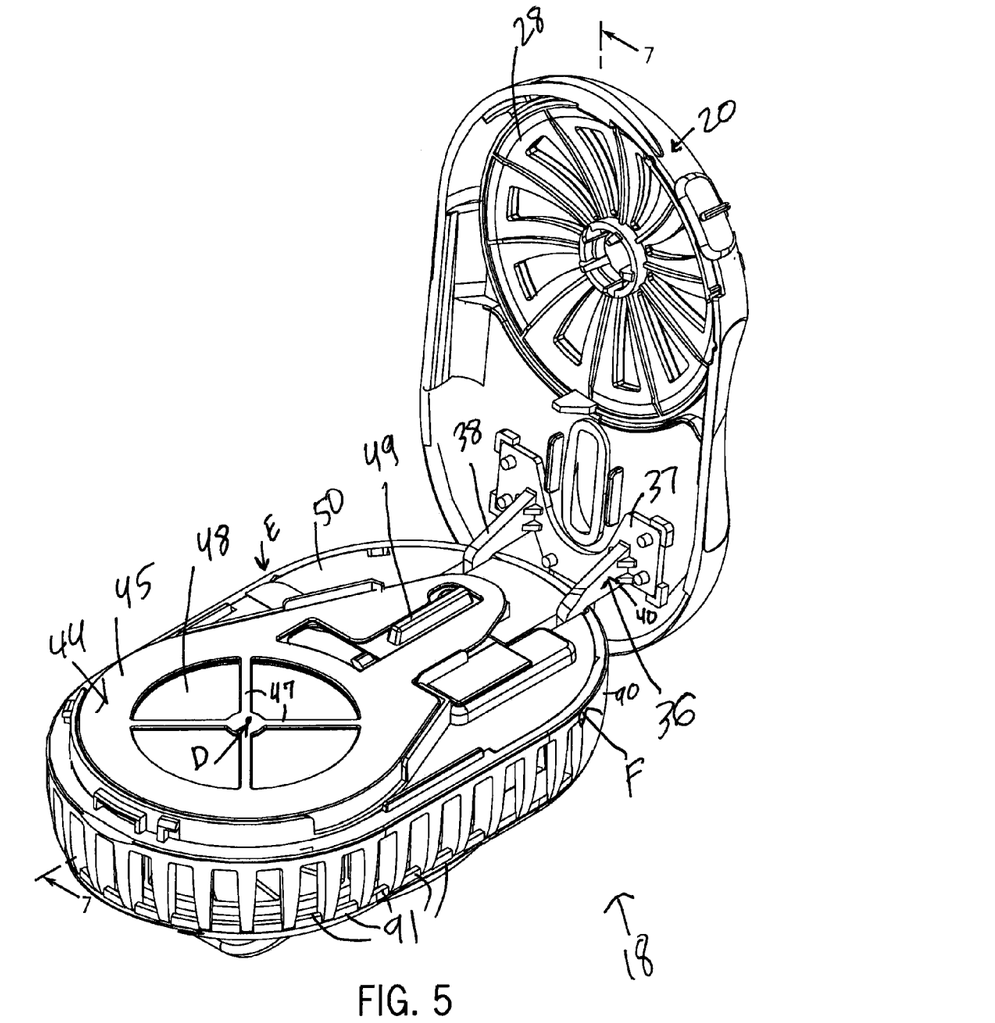
FIG. 5 is a right, bottom perspective view of the dispenser of FIG. 1 with the lid in an open position.
Figure 6:
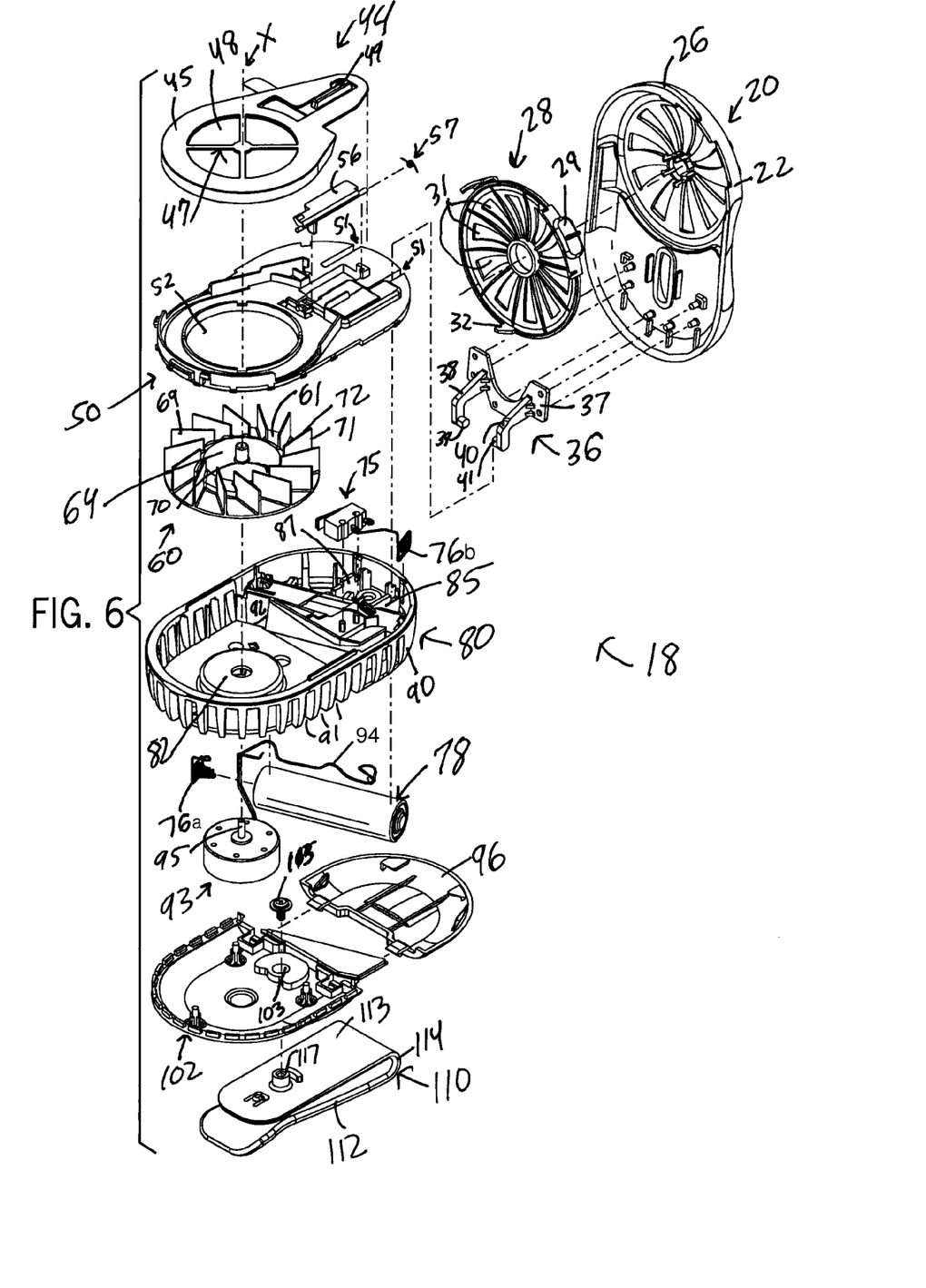
FIG. 6 is an exploded perspective view of the dispenser of FIG. 1.

The wearable chemical dispenser 18 also includes a hinge bracket 36 that is mounted to an inner surface of the top housing section 20 as shown in FIG. 5. The hinge bracket 36 has a flat base plate 37 that mounts to the top housing section 20, a generally L-shaped arm 38 having an inwardly directed pivot pin 39 at its end, and generally L-shaped arm 40 having an inwardly directed pivot pin 41 at its end. The arm 38 and the arm 40 are spaced apart on the plate 37 as shown in FIGS. 5 and 6. The hinge bracket 36 forms part of a hinge mechanism as described below.

A replaceable refill unit 44 is provided with the wearable chemical dispenser 18. The refill unit 44 has a generally slab-like support structure 45. In top plan view, the refill unit 44 has an essentially tear-drop shaped overall appearance, with a generally circular portion at one end and a generally triangular portion at another end. There is a spoke support 47 across a circular opening through the refill unit 44 (see FIG. 5). Across the spoke support 47 is positioned a fabric substrate 48. When air is drawn in, the air passes through the fabric substrate 48. The choice of the fabric, and its porosity, the speed of the air flow, and the vapor pressure of the active ingredient, are the main factors in coordinating the speed of use up of the active with the speed of use up of a visual use-up cue 49 (see FIG. 5) that can be viewed through the slot 25 of the top housing section 20. An example refill unit has a twelve hour life, and the visual use-up cue 49 is designed to evaporate or change in appearance after twelve hours. Button 56 covers use-up cue's evaporating surface when the device is off to prevent its indicator fluid from volatizing when the fan is not operating. This improves the accuracy of the use-up cue. A suitable visual use-up cue is described in U.S. Pat. No. 7,892,487.

By impregnating the fabric substrate 48 with an appropriate air treatment chemical, air entering the device will pick up some of the volatile chemical, and dispense it out of the device. Active release rates of 0.2 milligrams per hour (mg./hr.) or higher are preferred. Particularly preferred active ingredients are transfluthrin, prallethrin, vaporthrin, tefluthrin, and esbiothrin or other synthetic pyrethroids. For use in controlling mosquitoes, it is preferred to use metofluthrin from the Sumitomo Chemical Company (trade name SumiOne) as the active. The impregnation material can be pure active, or for ease of handling the material can be dissolved in a hydrocarbon or other solvent. Alternatively, or in addition, the fabric may also bear a fragrance, a deodorizer, or other air treatment chemical. It is preferred to have the fabric substrate 48 configured so that the pressure drop across the substrate is no more than 40 Pascals (Pa). Suitable fabrics can be made of woven or non-woven materials providing only minimal resistance to the airflow.

The fabric substrate 48 should also be capable of holding active ingredient dosed onto the material and also allow ready migration of the active to the surface so as to allow its evaporation in response to the airflow. For an active ingredient that is hydrophobic and migrateable at common environmental temperatures between about 10° C. and 40° C. (e.g., metofluthrin), suitable materials include, only by way of example, polyester, polypropylene, cotton, cellulose, poly-rayon, and other similar fabrics. These can be non-wovens with basis weights ranging from 10 grams per square meter (gsm) to 40 grams per square meter (gsm), fabricated from synthetic, natural, or combined synthetic and natural polymeric materials.

The ideal fabric substrate 48 should also allow for wicking of the active ingredient following dosing so as to ensure efficient distribution throughout the substrate, and thereafter allow migration of active ingredient to the substrate surface to replenish the active ingredient that is being evaporated by the passing airflow. Dosing may be by dropping, spraying, printing, or other conventional delivery of a liquid active ingredient to the substrate. A particularly desirable fabric is a non-woven felted material with a basis weight of 20-30 gsm fabricated from polyethylene terephthalate.

A frame 50 is located below the refill unit 44 in the wearable chemical dispenser 18. The frame 50 has a generally oblong perimeter, and supports the refill unit 44 (see FIGS. 5 and 6). Note that one side of the essentially triangular portion of the refill unit 44 is straight and the other is indented. This slight lack of symmetry is designed to accommodate a corresponding slight lack of symmetry along the top side of frame 50, and to thereby prevent a consumer from installing the refill unit 44 inside-out on the frame 50. One end of the frame 50 has a pair of slots 51 that form part of a hinge mechanism as described below. A circular opening 52 is provided at the other end of the frame 50. Holes in the frame 50 support a rotating activation button 56 that is biased by a rotary spring 57 into an off position.

Figure 7:
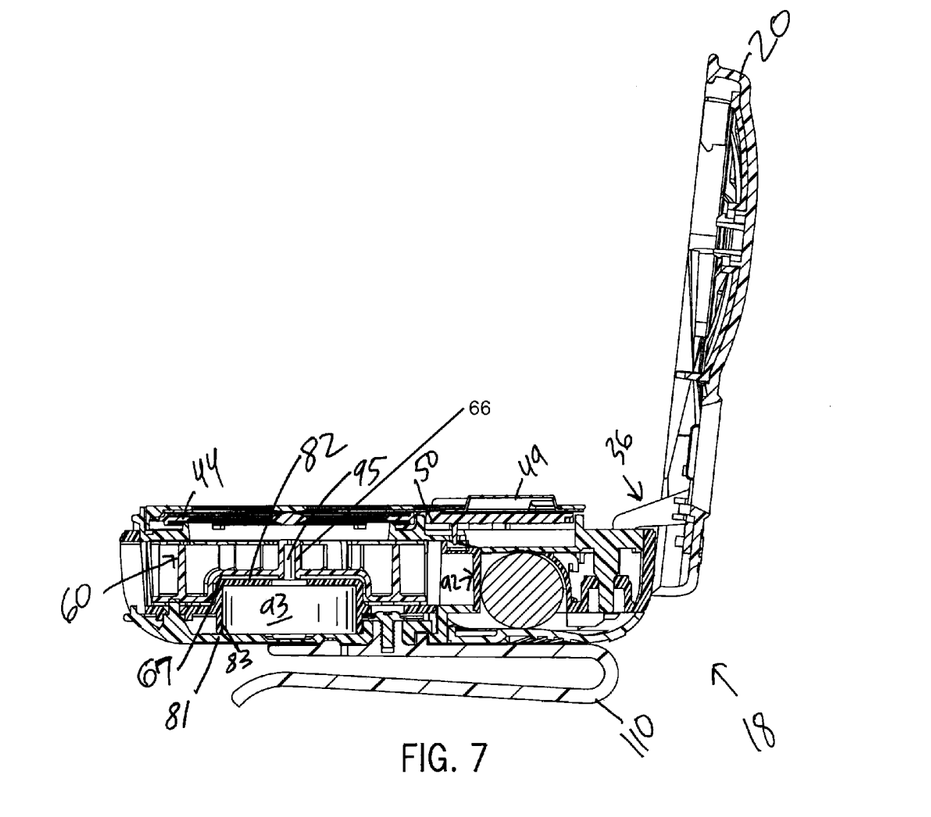
FIG. 7 is a cross-sectional view taken along line 7-7 of FIG. 5.
Figure 8:
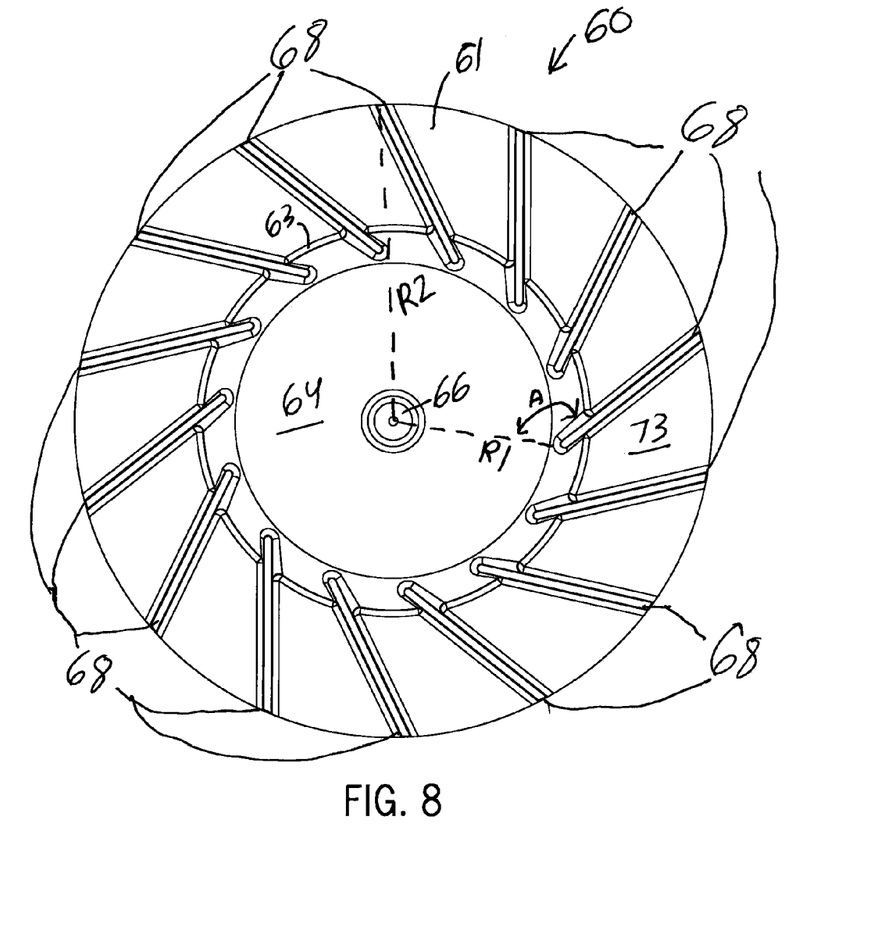
FIG. 8 is a top view of the rotor fan of the dispenser of FIG. 1.

Looking at FIGS. 6 and 8, there is shown a fan 60 of the wearable chemical dispenser 18. The fan 60 has a rotor 61 having a central vertical wall 63 that joins a top central horizontal wall 64. The central vertical wall 63 and the top horizontal wall 64 define a recess 67 in the bottom of the rotor 61 (see FIG. 7). The top horizontal wall 64 of the rotor 61 includes a tubular mounting element 66 on the axis of the rotor 61.

The preferred fan 60 includes fourteen fan blades 68 (see FIG. 8). It has been discovered that a fan configuration, which results in an ideal balance of airflow and minimal power consumption for the wearable chemical dispenser 18, includes twelve to eighteen fan blades. Preferably, the fan produces an average volumetric flow rate of air of 1.5 to 3 cubic feet per minute (with the refill unit 44 installed) over the life (e.g., at least eight, and most preferably at least twelve hours) of a refill unit 44. Typically, the fan will operate at 3000-5000 rpm. In one example wearable chemical dispenser 18, over the life (e.g., twelve hours) of a refill unit 44, the consumed power from the power supply is 0.20 watts or less. In one example embodiment, over a twelve hour life of a refill unit 44, the consumed power from the power supply is about 0.19 watts while maintaining an average volumetric flow rate of air of at least 1.6 cubic feet per minute over the twelve hour period. When using a battery for the power supply, the voltage will vary during discharge. However, the power consumed can be determined from the total energy consumed divided by the total time.

Each blade 68 has a generally rectangular body 69 defined by an inner edge 70, an outer edge 71, a top edge 72 extending from the inner edge 70 to the outer edge 71, and top surface 73 of the rotor 61. It has been discovered that a fan configuration, which results in an ideal balance of airflow and minimal power consumption for the wearable chemical dispenser 18, includes a range of fan sizes and fan blade angles. Preferably, each blade 68 has a length extending from the inner edge 70 to the outer edge 71 in which the length measures 80% to 130% of the distance of radial reference line R1. Preferably, each blade 68 has a length extending from the inner edge 70 to the outer edge 71 in which the length measures 45% to 75% of the distance of radial reference line R2. Preferably, the included angle A in FIG. 8, which is formed between the body 69 of each blade 68 and its associated radial reference line $R_1$, is in the range of 100 to 150 degrees. These example fan sizes and fan blade angles contribute to an ideal balance of airflow and minimal power consumption for the wearable chemical dispenser 18. Thus, among other things, the average volumetric flow rate of air from the fan depends on the outer radius of the rotor, the inner radius of the rotor, the number of blades, the blade angles, and the fan revolutions per minutes.

One non-limiting example of the fan 60 has a length extending from the inner edge 70 to the outer edge 71 of about 15 millimeters, a radial reference line R1 of about 14 millimeters, a radial reference line R2 of about 25 millimeters, and an included angle A of about 120 degrees. In this non-limiting example, blade thicknesses can range from 0.3-1.0 millimeters, with 0.6 millimeters being preferred, and blade height (from the top surface 73 of the rotor 61 to the top edge 72 of the body 69) can range from 5-11 millimeters, with about 8 millimeters being preferred.

The wearable chemical dispenser 18 includes an electrical power supply. In the example embodiment shown, a microswitch 75 of the power supply is electrically connected to battery contacts 76*a* to complete an electrical circuit with battery 78 and the battery contacts 76*b* to provide electricity to the microswitch 75. When a user rotates the slide cover 28 by rotating the on-off button 29 into the 'on' position, the cam projection 32 of the slide cover 28 is driven into the rotating activation button 56 which then contacts the microswitch 75 to turn on the power supply.

Looking at FIGS. 6-7 and 9-12, the wearable chemical dispenser 18 includes a chassis 80 for mounting various components of the wearable chemical dispenser 18 and for contributing to the control of air flow from the dispenser 18. When the top housing section 20 and the chassis 80 are in a closed position (see, e.g., FIG. 1), a housing having an interior space is formed. The chassis 80 engages the frame 50 in a snap fit.

The chassis 80 has a bottom wall 81 with a raised portion 82 that defines a upwardly directed space 83 in the chassis 80 (see FIGS. 6 and 7). A battery recess 84 for a single AA battery is also provided in the bottom wall 81 of the chassis 80 (see FIG. 7). The battery contacts 76*a*, 76*b* are mounted at opposite ends of the battery recess 84. Extending upward from the bottom wall 81 of the chassis 80 there is a hinge support 85 and a hinge support 87. The hinge mechanism allows a user to open the top housing section 20 to the open position of FIG. 7 so that a new refill unit 44 can be installed on the frame 50 as shown in FIG. 5. The pivot pin 39 of the hinge arm 38 moves in a notch of the hinge support 87. The pivot pin 41 moves in a notch of the hinge support 85 in a similar manner. During movement of the hinge, the arm 38 and the arm 40 of the hinge bracket 36 move in the slots 51 of the frame 50 (see FIG. 5). The configuration of the pivot pins 39, 41 of the arms 38, 40 of the hinge bracket 36 provides an advantageous hinging action when opening and closing the top housing section 20.

The chassis 80 also includes a side wall 90 having regularly spaced openings 91 that define outlets for permitting air mixed with air treatment chemical to exit the interior space of the wearable chemical dispenser 18. In the non-limiting example embodiment shown in FIG. 4, the openings 91 extend from point E to point F around the side wall 90 of the chassis 80. One non-limiting example of the total outlet area of the openings 91 is $8.5\times10^{-4}$ $m^2$. Preferably, each opening 91 is of generally uniform area.

Looking at FIGS. 9-12, some of the features that provide for improved air flow in the dispenser 18 can be explained further. The side wall 90 of the chassis 80 includes a first side wall section 90*a* on a first side $S_1$ of a longitudinal axis H of the chassis 80, a second side wall section 90*b* on a second side $S_2$ of the longitudinal axis H of the chassis 80, a first end wall section 90*c* connecting the first side wall section 90*a* and the second side wall section 90*b*, and a second end wall section 90*d* connecting the first side wall section 90*a* and the second side wall section 90*b*. The outlets that permit air mixed with air treatment chemical to exit the interior space of the wearable chemical dispenser 18 can be grouped into a first array 91*a* of openings on the first side $S_1$ of a longitudinal axis H of the chassis 80 and a second array 91*b* of openings on the second side $S_2$ of the longitudinal axis H of the chassis 80. The first array 91*a* of openings and the second array 91*b* of openings are non-symmetric about the longitudinal axis H due to three additional openings 91*b*' in the second side wall section 90*b* (see FIG. 12). Each opening of the first array 91*a* of openings and the second array 91*b* of openings are preferably of generally uniform area.

Figures 9, 10:
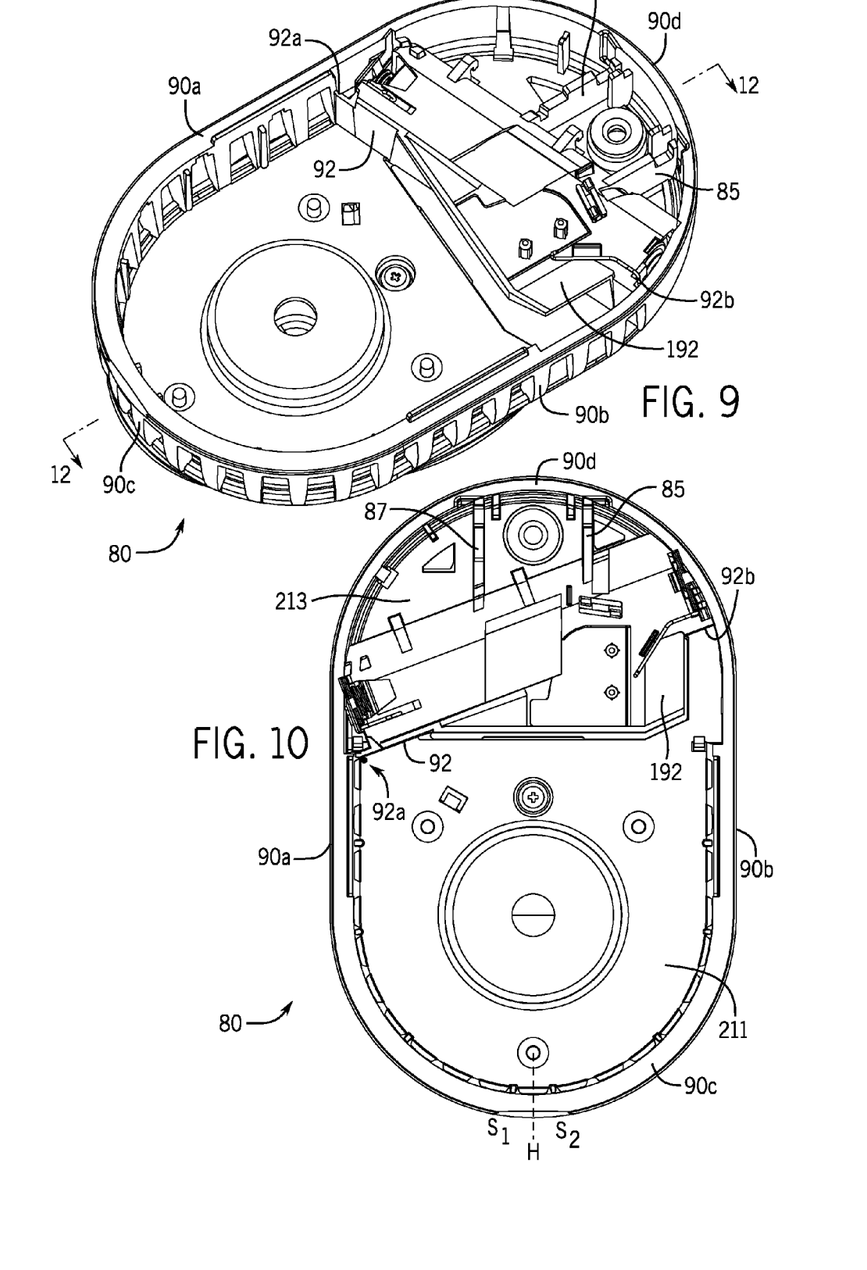
FIG. 9 is a right perspective view of the chassis of the dispenser of FIG. 1.
FIG. 10 is a top plan view of the chassis of the dispenser of FIG. 1.
Figure 12:
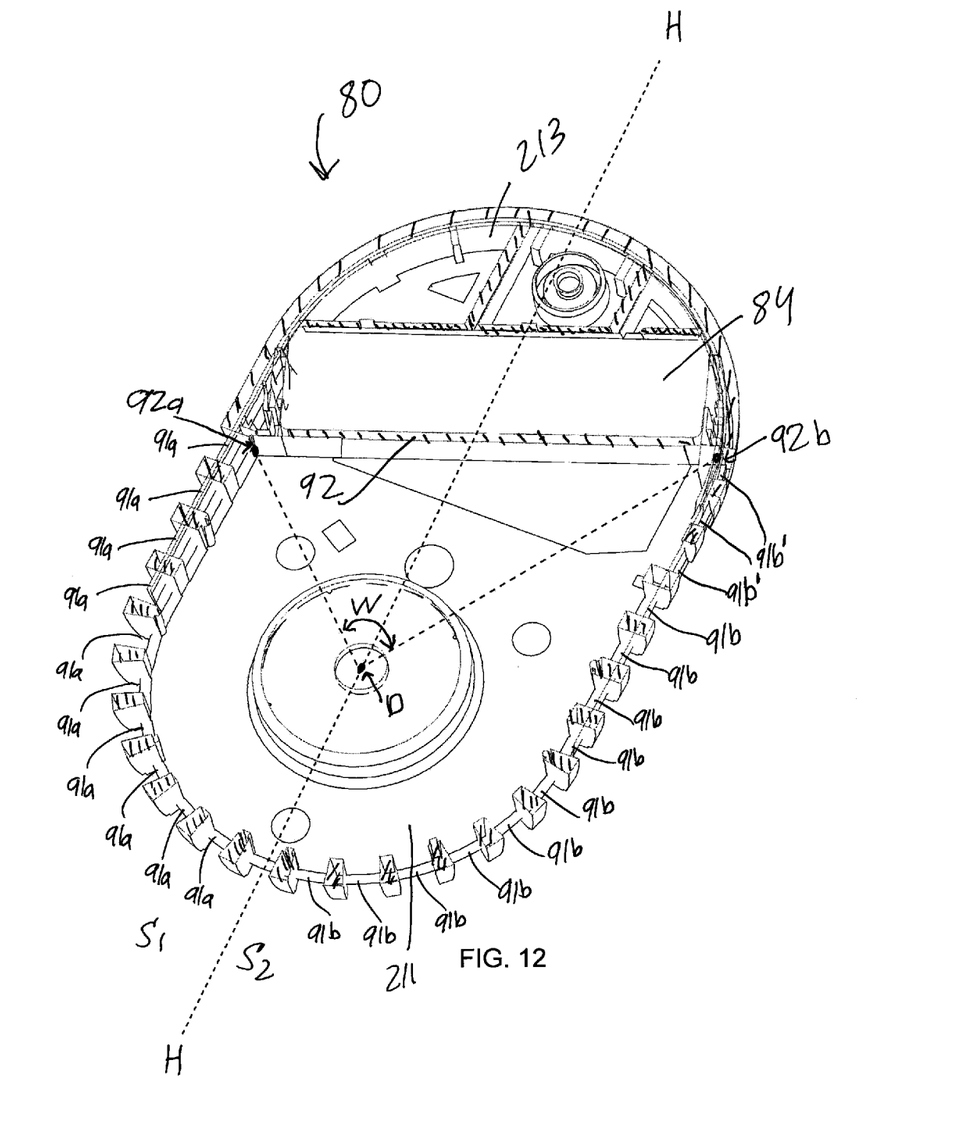
FIG. 12 is a cross-sectional view of the chassis of the dispenser taken along line 12-12 of FIG. 9.

Looking at FIGS. 10 and 12, a straight partition wall 92 creates a fan compartment 211 and a power supply compartment 213. The partition wall 92 and a major axis of the battery recess 84 are both oriented at an oblique angle to the longitudinal axis H of the chassis 80. An overhang 192 (see FIGS. 9 and 10) creates a flow director over the partition wall 92. A first end 92*a* of the partition wall 92 terminates at the first side wall section 90*a* of the chassis 80 and an opposite second end 92*b* of the partition wall 92*b* terminates at the second end wall section 90*b* of the chassis 80. The first end 92*a* of the partition wall 92 terminates near point E in FIG. 4, and the second end 92*b* of the partition wall 92*b* terminates near point F in FIG. 4. As shown in FIG. 12, an included angle W is defined by (i) the first end 92*a* of the partition wall 92, (ii) a rotational axis D of the fan 60, and (iii) the second end 92*b* of the partition wall 92. Preferably, the included angle W is less than 90 degrees. In some non-limiting embodiments, the included angle W is in the range of 45-89 degrees, or the included angle W is in the range of 60-89 degrees, or the included angle W is in the range of 70-89 degrees, or the included angle W is in the range of 80-89 degrees.

Due to the first array 91*a* of openings and the second array 91*b* of openings ending adjacent the first end 92*a* and the second end 92*b* of the partition wall 92 respectively, and the orientation of the first end 92*a* and the second end 92*b* of the partition wall 92 to create the included angle W of less than 90 degrees, the mixture of air and air treatment chemical delivered through the openings 91 to outside of the housing has an ejection angle of greater than 270 degrees, or greater than 280 degrees, or greater than 290 degrees, or greater than 300 degrees, or greater than 310 degrees, or greater than 320 degrees. Thus, among other things, the angled straight partition wall 92 creates an advantageous flow path in the dispenser 18.

Preferably, a flow path from the fan 60 to the openings 91 is unobstructed. Some other devices included a slide cover designed to shut off air flow by blocking the inlet vents and the exhaust vents. The intent was to minimize loss of actives while the unit is not in use by blocking off airflow across the dosed pad. The walls blocking the exhaust vents and the geometries supporting them occupied large space and caused the device to increase in size. These blocking walls are eliminated in the dispenser 18 without increased loss in actives ingredient. Also, the battery recess 84 is isolated from the openings 91. These example opening configurations contribute to an ideal balance of airflow and minimal power consumption for the wearable chemical dispenser 18.

Looking at FIGS. 6 and 7, a motor 93 is positioned in the space 83 in the chassis 80, and a wire 94 connects the motor 93 to the microswitch 75 for powering the motor when the rotating activation button 56 contacts the microswitch 75 to turn on the power supply. The motor 93 includes a drive shaft 95 that is connected to the tubular mounting element 66 on the rotor 61. As a result, the motor 93 can rotate the fan 60. A battery door 96 (see FIG. 11) covers the battery recess 84 in the bottom wall 81 of the chassis 80. The battery door 96 includes mounting tabs 97. A bottom cover 102 is fastened to the chassis 80 by way of a fastener such as posts on cover 102 which penetrate through holes in chassis 80 and whose ends are heat staked.

Figure 11:
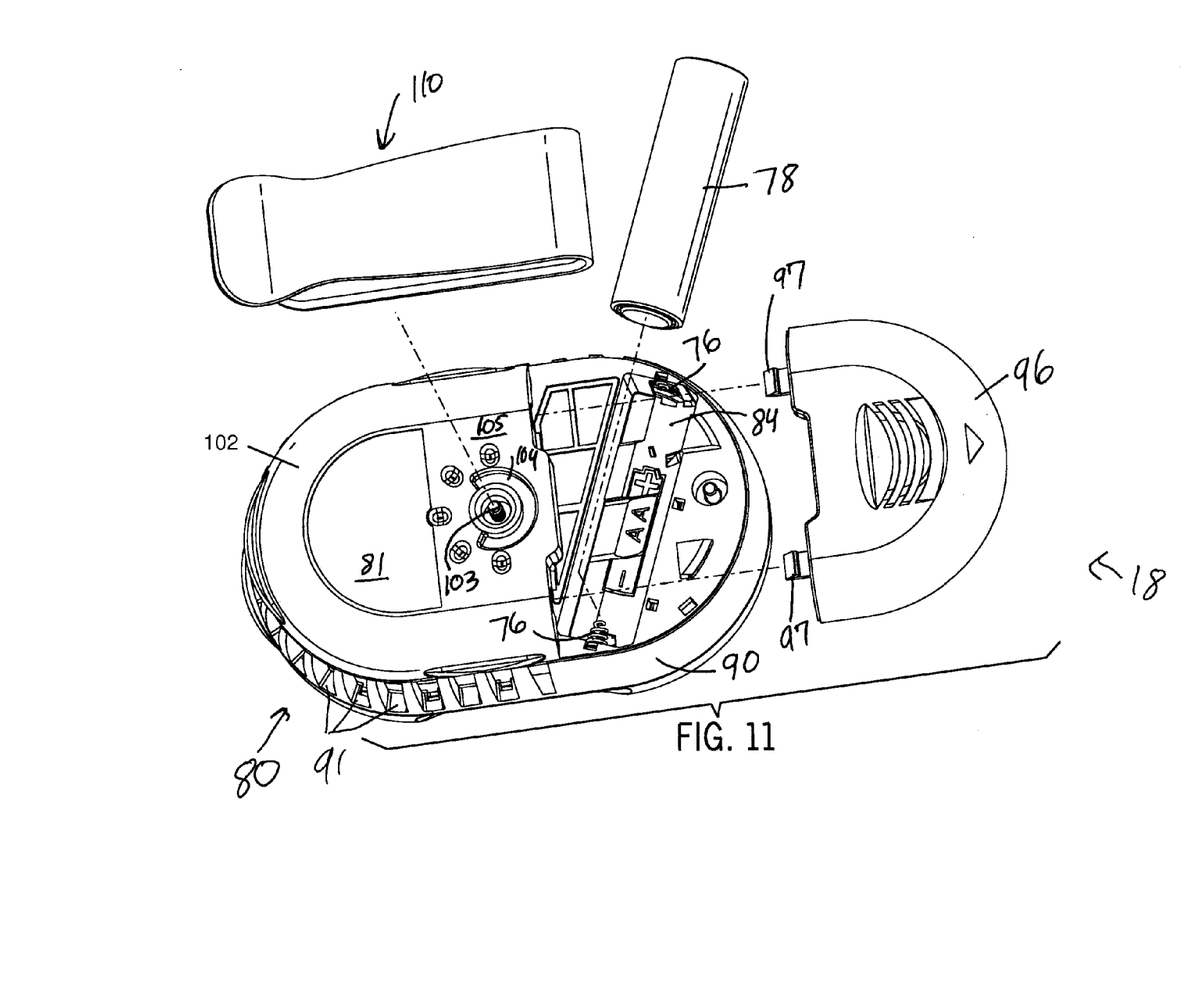
FIG. 11 is a bottom perspective view of the chassis of the dispenser of FIG. 1.

Looking now at FIGS. 6 and 11, means for clipping the wearable chemical dispenser 18 to a user's clothing (e.g., a belt) are shown. The bottom cover 102 includes a throughhole 103 partially surrounded by an arcuate well 104 in a bottom surface 105 of the bottom cover 102. The wearable chemical dispenser 18 also includes a clip 110 having a front section 112 that is spaced at its upper end from a rear section 113 by a top section 114 that connects the front section 112 and the rear section 113. At the lower end of the clip 110, the front section 112 and the rear section 113 may be in contact until flexed apart by a user. The rear section 113 of the clip 110 has a tubular mounting element 117. A fastener 115 (see FIG. 6) is inserted through the throughhole 103 of the bottom cover 102 and into the tubular mounting element 117 of the clip 110 to connect the bottom cover 102 and the clip 110 such that the clip 110 can rotate.

Regarding component construction, the top housing section 20, slide cover 28, hinge bracket 36, support structure 45 of the refill unit 44, frame 50, fan 60, chassis 80, battery door 96, bottom cover 102, and clip 110 may be formed from a suitable polymeric material such as polyethylene, polypropylene, or polyester.

In operation, the wearable chemical dispenser 18 will be clipped on a belt, purse or the like using clip 110 for that purpose. When a user moves the on-off button 29 along the side wall 22 of the top housing section 20 into the 'on' position, the openings 31 of the slide cover 28 align with the apertures 24 that are radially arranged in the top wall 23 of the top housing section 20. The cam projection 32 of the slide cover 28 is driven into the rotating activation button 56 which then contacts the microswitch 75 to turn on the power supply to power the fan 60 by way of motor 93. Air is sucked by the fan 60 of the wearable chemical dispenser 18 in through apertures 24 and the openings 31. As the air passes through fabric substrate 48, the air treatment chemical mixes into the air and a mixture of air and air treatment chemical is then blown radially out openings 91 (preferably down along pants or dresses). A user can rotate the clip 110 as described above to change the path of the mixture of air and air treatment chemical.

While the present device is primarily intended to be used as a wearable item carried with a human when outdoors, it can also be laid flat, with the clip 110 downward and the top housing section 20 upward, on a picnic table or the like. When used in this manner it can provide protection to an area during a picnic or similar outdoor activity.

Hence, the device is much more compact and lightweight, yet still effective. Further, the cost of operation from a battery standpoint is reduced. The device can more comfortably be used when seated, and provides greater control over dispensing direction. Also, installing a replacement active refill is easier. These advantages are achieved at lowered cost, and provide a reliable construction.

In the wearable dispenser, the intake grill size is designed to work in concert with an improved fan which falls within a specific range of fan blades, size and blade angle. A low current draw motor is recessed into the axial hub of the fan design. The airflow exits through greater than 270 degrees of output vents. This combination of design features results in an ideal balance of airflow and minimal power consumption that results in a highly efficient system, which produces good insect repellency and usage duration in a relatively small, lightweight unit.

Example

The following Example has been presented in order to further illustrate the invention and is not intended to limit the invention in any way.

A comparative study was conducted in glass chambers using *culex quinquefasciatus* (mosquitoes) and *aedes aegypti* (mosquitoes). A chemical dispenser according to U.S. Patent Application Publication No. 2011/0038761 and one of each of the two types of mosquitoes were introduced into separate chambers at the same time. A chemical dispenser according to FIGS. 1-12 described herein and one of each of the two types of mosquitoes were also introduced into separate chambers at the same time. All of the chemical dispensers had the same type and the same amount of insect control active ingredient. The chemical dispensers were turned on, and all of the chemical dispensers had an initial volumetric flow rate of air of 1.6 cubic feet per minute. Knockdown percentage data was collected for at least five minute time intervals for the first sixty minutes and for at least ten minute time intervals for the second sixty minutes. Knockdown data was collected until 100% knockdown was achieved, or until the expiration of 120 minutes. The study showed no statistically significant knockdown change for either mosquito type using fresh or twelve hour aged batteries in the chemical dispenser according to U.S. Patent Application Publication No. 2011/0038761 and a chemical dispenser according to the invention. The chemical dispensers according to U.S. Patent Application Publication No. 2011/0038761 had an volumetric flow rate of air of 1.6 cubic feet per minute for twelve hours. The chemical dispensers according to FIGS. 1-12 described herein had an volumetric flow rate of air of 1.6 cubic feet per minute for twelve hours.

Without intending to be bound by theory, it is believed that the improved air flow characteristics of a chemical dispenser according to the invention unexpectedly overcome the energy loss in changing from two AAA batteries (as in the dispenser of U.S. 2011/0038761) to one AA battery (as in the present invention). In this regard, energy tables for alkaline long life batteries show an AA battery as having an average voltage during discharge of 1.225, a milli-amp hours rating of 2122, a watt-hours rating of 2.60, and a joules rating of 9360, and an AAA battery as having an average voltage during discharge of 1.225, a milli-amp hours rating of 1150, a watt-hours rating of 1.41, and a joules rating of 5071. Note that the AA battery has ratings less than twice the reported values for an AAA battery (i.e., two AAA batteries were used in the dispenser of U.S. 2011/0038761) and therefore, there is an energy loss in changing from two AAA batteries (as in the dispenser of U.S. 2011/0038761) to one AA battery (as in the present invention).

Thus, it has been discovered that the invention enhances energy efficiency allowing the usage of one AA battery instead of two AAA batteries while providing the same efficacy and longer life as compared to prior devices. In the non-limiting example of the present invention tested, the use of a single repositioned battery allows for three additional vents on the downstream side of the fan, resulting in improved air-flow flow leading to a better performing device and a higher air ejection angle (greater than 270 degrees) at a lower energy cost (i.e., one AA battery). In contrast, a chemical dispenser according to U.S. Patent Application Publication No. 2011/0038761 exhibits an air ejection angle of about 255 degrees and uses two AAA batteries.

While an example embodiment has been described above, it should be appreciated that there are numerous other embodiments of the invention within the spirit and scope of this disclosure. For example, the device can be powered by a different source of energy (e.g. a solar power panel), other forms of actives can be dispensed along with or in substitution for the insect control ingredients (e.g. a fragrance or deodorizing chemical), and even when an insect control ingredient is dispensed it need not be one focused on controlling mosquitoes (e.g., chemicals for repelling other flying or crawling insects or pests can be used). Hence, the invention is not to be limited to just the specific embodiments shown or described.

INDUSTRIAL APPLICABILITY

Provided herein are wearable dispensing devices capable of dispensing insect control chemicals and/or other air treatment chemicals adjacent a human body.

All documents cited in the Detailed Description of the Invention are, in relevant part, incorporated herein by reference; the citation of any document is not to be construed as an admission that it is prior art with respect to the present invention.

What is claimed is:

1. A wearable device for dispensing an air treatment chemical, the device comprising:
a housing including an inlet for permitting air to enter into an interior space of the housing and including a plurality of spaced apart outlets for permitting air mixed with air treatment chemical to exit the interior space;
a substrate positioned within the housing, the substrate bearing an air treatment chemical;
a power supply mounted within a power supply compartment of the housing; a motor mounted within the housing, the motor being powered by the power supply; and
a fan mounted within a fan compartment of the housing and connected to the motor, the fan being capable of moving air from the inlet adjacent the substrate so as to mix air treatment chemical into the moving air, and then deliver a mixture of air and air treatment chemical through the outlets to outside of the housing,
wherein the outlets are in fluid communication with the fan compartment of the housing, and
wherein the outlets comprise a first array of openings on a first side of a longitudinal axis of the housing and the outlets also comprise a second array of openings on an opposite second side of the longitudinal axis of the housing, the first array of openings and the second array of openings being non-symmetric about the longitudinal axis of the housing;
wherein the first array of openings extends continuously from the longitudinal axis of the housing to a partition wall between the fan compartment and the power supply compartment, and
wherein the second array of openings extends continuously from the longitudinal axis of the housing to the partition wall.

2. The device of claim 1 wherein:
the housing comprises a first side wall section on the first side of the longitudinal axis of the housing, a second side wall section on the second side of the longitudinal axis of the housing, a first end wall section connecting the first side wall section and the second side wall section, and a second end wall section connecting the first side wall section and the second side wall section,
the first array of openings is located in the first side wall section and the first end wall section of the housing,
the second array of openings is located in the second side wall section and the first end wall section of the housing.

3. The device of claim 2 wherein:
the fan compartment is defined by the first side wall section of the housing, the second side wall section of the housing, the first end wall section of the housing, and a partition wall between the fan compartment and the power supply compartment, and
a first end of the partition wall terminates at the first side wall section of the housing and an opposite second end of the partition wall terminates at the second end wall section of the housing.

4. The device of claim 3 wherein:
the first side wall section and the second side wall section of the housing are generally straight, and
the first end wall section and the second end wall section of the housing are generally curved.

5. The device of claim 3 wherein:
the first array of openings and the second array of openings are of generally uniform area.

6. The device of claim 3 wherein:
an included angle is defined by (i) a first location where the first end of the partition wall terminates at the first side wall section of the housing, (ii) a rotational axis of the fan, and (iii) a second location where the second end of the partition wall terminates at the second end wall section of the housing, and
the included angle is less than 90 degrees.

7. The device of claim 1 wherein:
the fan compartment and the power supply compartment are in a side by side relationship coplanar with the longitudinal axis of the housing.

8. The device of claim 1 wherein:
the power supply compartment includes a recess for receiving the power supply, the recess having a major axis oriented at an oblique angle to the longitudinal axis of the housing.

9. The device of claim 8 wherein:
the power supply is a single AA sized battery, and
the recess is dimensioned to receive the battery.

10. The device of claim 1 wherein:
the mixture of air and air treatment chemical delivered through the outlets to outside of the housing has an ejection angle of greater than 270 degrees.

11. A wearable device for dispensing an air treatment chemical, the device comprising:
a housing including an inlet for permitting air to enter into an interior space of the housing and including a plurality of spaced apart outlets for permitting air mixed with air treatment chemical to exit the interior space;
a substrate positioned within the housing, the substrate bearing an air treatment chemical;
a power supply mounted within a power supply compartment of the housing;
a motor mounted within the housing, the motor being powered by the power supply; and a fan mounted within a fan compartment of the housing and connected to the motor, the fan being capable of moving air from the inlet adjacent the substrate so as to mix air treatment chemical into the moving air, and then deliver a mixture of air and air treatment chemical through the outlets to outside of the housing, a partition wall between the fan compartment and the power supply compartment;

wherein the outlets are in fluid communication with the fan compartment of the housing, and wherein the power supply compartment includes a recess for receiving the power supply, and the partition wall is oriented at an oblique angle to a longitudinal axis of the housing, wherein the outlets comprise a first array of openings extending continuously from the longitudinal axis of the housing to the partition wall, and wherein the outlets also comprise a second array of openings extending continuously from the longitudinal axis of the housing to the partition wall.

12. The device of claim 11 wherein:
the power supply is a single AA sized battery, and
the recess is dimensioned to receive the battery.

13. The device of claim 12 wherein:
the device can maintain an average volumetric flow rate of air of at least 1.5 cubic feet per minute over a twelve hour period.

14. The device of claim 11 wherein:
the mixture of air and air treatment chemical delivered through the outlets to outside of the housing has an ejection angle of greater than 270 degrees.

15. The device of claim 11 wherein:
the fan compartment is defined by the first side wall section of the housing, the second side wall section of the housing, the first end wall section of the housing, and the partition wall between the fan compartment and the power supply compartment, and
a first end of the partition wall terminates at the first side wall section of the housing and an opposite second end of the partition wall terminates at the second end wall section of the housing,
an included angle is formed by (i) a first location where the first end of the partition wall terminates at the first side wall section of the housing, (ii) a rotational axis of the fan, and (iii) a second location where the second end of the partition wall terminates at the second end wall section of the housing, and
the included angle is less than 90 degrees.

16. A wearable device for dispensing an air treatment chemical, the device comprising:
a housing including an inlet for permitting air to enter into an interior space of the housing and including a plurality of spaced apart outlets for permitting air mixed with air treatment chemical to exit the interior space;
a substrate positioned within the housing, the substrate bearing an air treatment chemical;
a power supply mounted within a power supply compartment of the housing; a motor mounted within the housing, the motor being powered by the power supply; and
a fan mounted within a fan compartment of the housing and connected to the motor, the fan being capable of moving air from the inlet adjacent the substrate so as to mix air treatment chemical into the moving air, and then deliver a mixture of air and air treatment chemical through the outlets to outside of the housing,
wherein the fan compartment is defined by a first side wall section of the housing, a second side wall section of the housing, an end wall section of the housing, and a partition wall between the fan compartment and the power supply compartment,
wherein the outlets comprise a first array of openings in the first side wall section of the housing and a second array of openings in the second side wall section of the housing, the openings being in fluid communication with the fan compartment of the housing, and
wherein the partition wall is dimensioned such that the fan compartment is in fluid communication with an additional number of openings in the second side wall section of the housing compared to the first side wall section of the housing,
wherein the first array of openings extends continuously from the longitudinal axis of the housing to the partition wall, and
wherein the second array of openings extends continuously from the longitudinal axis of the housing to the partition wall.

17. The device of claim 16 wherein:
the partition wall is a straight wall oriented at an oblique angle to a longitudinal axis of the housing.

18. The device of claim 17 wherein:
the power supply compartment includes a recess for receiving the power supply, the recess having a major axis oriented at the oblique angle to the longitudinal axis of the housing.

19. The device of claim 16 wherein:
a first end of the partition wall terminates at the first side wall section of the housing and an opposite second end of the partition wall terminates at the second end wall section of the housing,
an included angle is defined by (i) a first location where the first end of the partition wall terminates at the first side wall section of the housing, (ii) a rotational axis of the fan, and (iii) a second location where the second end of the partition wall terminates at the second end wall section of the housing, and
the included angle is less than 90 degrees.

20. The device of claim 16 wherein:
the mixture of air and air treatment chemical delivered through the outlets to outside of the housing has an ejection angle of greater than 270 degrees.

* * * * *